United States Patent [19]

Wei et al.

[11] Patent Number: 5,482,930
[45] Date of Patent: Jan. 9, 1996

[54] ANTI-INFLAMMATORY COMPOSITION AND METHOD WITH DES-TYR DYNORPHIN AND ANALOGUES

[75] Inventors: Edward T. Wei, Berkeley, Calif.; Holly A. Thomas, Wilmette, Ill.

[73] Assignee: The Regents of the University of California, Oakland, Calif.

[21] Appl. No.: 74,210

[22] Filed: Jun. 9, 1993

[51] Int. Cl.$^6$ .............................. A61K 38/00; C07K 7/00; C07K 7/06; C07K 7/08
[52] U.S. Cl. .............................. 514/13; 514/16; 530/326; 530/329
[58] Field of Search .............................. 514/16; 330/326, 330/329

[56] References Cited

U.S. PATENT DOCUMENTS

| | | |
|---|---|---|
| 4,361,553 | 11/1982 | Loh et al. |
| 4,396,606 | 8/1983 | Goldstein |
| 4,462,941 | 7/1984 | Lee et al. |
| 4,481,191 | 11/1984 | Wei et al. |
| 4,684,624 | 8/1987 | Hosobushi et al. |
| 5,177,060 | 1/1983 | Wei |

OTHER PUBLICATIONS

Fan, et al, *Brain Research*, vol. 623 (1), 1993.
U.S. Ser. No. 07/925081, filed Aug. 4, 1992, Wei et al.
Long et al., "Hindlimb Paralytic Effects of Prodynorphin–Derived Peptides Following Spinal Sub-arachnoid Injection in Rats," *European Journal of Pharmacology*, 153 (1988), pp. 45–54.
Takemori et al., "Suppression by Dynorphin A and [Des–Tyr$^1$]Dynorphin A Peptide of the Expression of Opiate Withdrawal and Tolerance in Morphine–Dependent Mice," *J. of Pharmacol. & Exper. Therap.*, 266(1), (1993), pp. 121–124.
Goldstein et al., "Nonopiate Effects of Dynorphin and Des–Tyr–Dynorphin," *Science*, 218 (10 Dec. 1982), pp. 1136–1138.
Wei et al., "Anti–Inflammatory Peptide Angonist," *Annu. Rev. Pharmacol. Toxicol.*, 33 (1993), pp. 91–108.
Wei et al., "Corticotropin–Releasing Factor Inhibits Neurogenic Plasma Extravasation in the Rate Paw," *J. of Pharmacol. & Exper. Therap.*, 238(3), pp. 783–787 (1986).
Wei et al., "Peptides of the Corticoliberin Superfamily Attenuate Thermal and Neurogenic Inflammation in Rat Pawskin," *European Journal of Pharmacology*, 168 (1989), pp. 81–86.

*Primary Examiner*—Jill Warden
*Assistant Examiner*—S. G. Marshall
*Attorney, Agent, or Firm*—Majestic, Parsons, Siebert & Hsue

[57] ABSTRACT

A method for treating inflammatory conditions is provided in which a peptide is administered in an amount effective to decrease inflammation, with the peptide having the sequence G-G-F-L-R-R-I-R-P-K-L-K-W-D-N-Q (SEQ ID NO:1), G-G-F-L-R-R-I-R-P-K-L-K-W-D-N-Q-NH$_2$ (SEQ ID NO:2), Ac-R-R-I-R-P-K-L-NH$_2$ (SEQ ID NO:3), or Ac-R-R-I-R-P-K-l-NH$_2$.

10 Claims, 1 Drawing Sheet

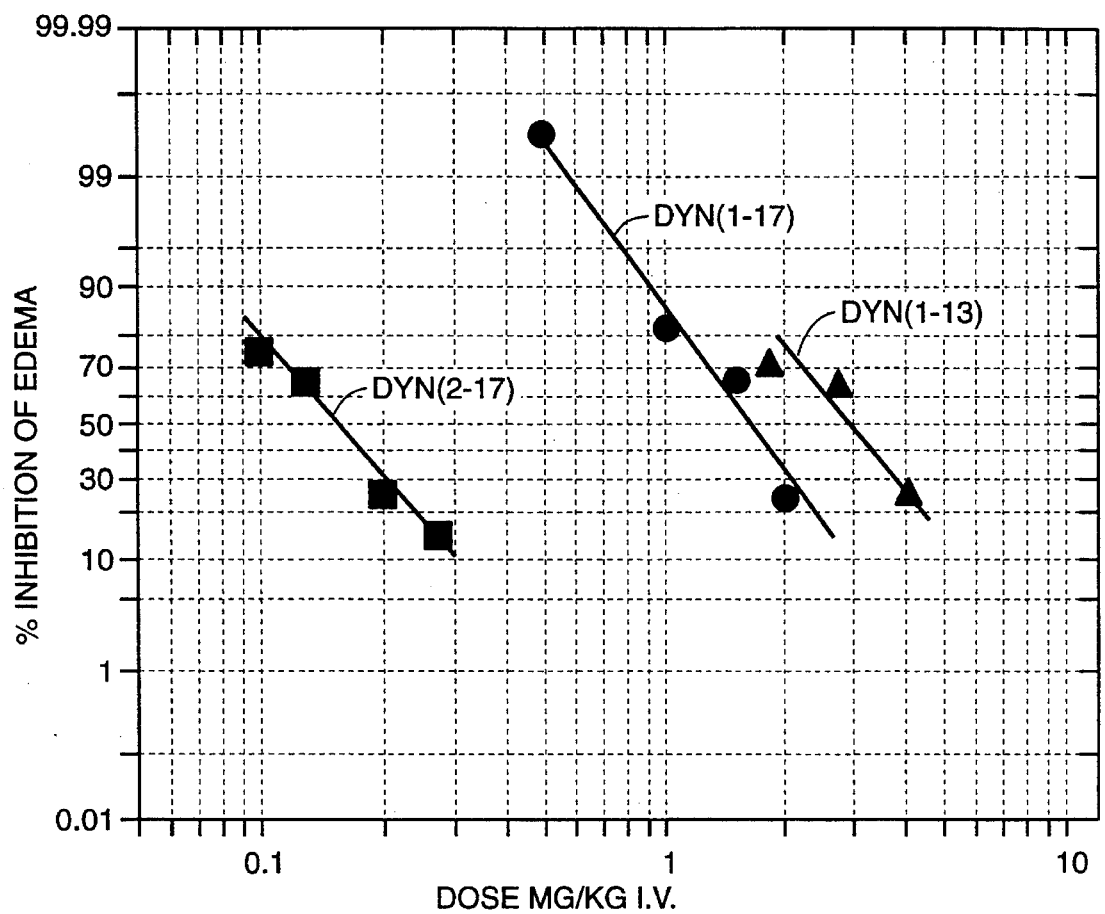
FIG._1

ANTI-INFLAMMATORY COMPOSITION AND METHOD WITH DES-TYR DYNORPHIN AND ANALOGUES

This invention was made with Government support under Grant No. DA-00091 awarded by the NIDA/US Public Health Services. The Government has certain rights in this invention.

FIELD OF THE INVENTION

This invention generally relates to compounds of the dynorphin family, but where the usual N-terminal tyrosine is missing, and more particularly relates to use of certain dynorphin A related compounds as anti-inflammatory agents.

BACKGROUND OF THE INVENTION

The vascular tree is a complex network of vessels designed to maintain, at its outermost subdivisions, a surface area between blood and tissues for the exchange of gases and nutrients and for the drainage of waste products. During the early stages of inflammation, the sensitive mechanisms relating to microvascular perfusion are altered so that vascular integrity is compromised, blood contents leak into tissues, and hemostasis may develop. In the whole organism, severe and abrupt injury to the microcirculation distorts tissue architecture, impedes delivery of oxygen to cells, and causes extensive fluid loss from the vascular compartment, leading to edema, electrolyte imbalance, shock, and other circulatory disorders. The search for and identification of agents that modulate the immediate responses of inflammation may generate drugs with clinical benefit.

Recent studies suggest that certain peptides act as agonists to inhibit inflammation, defined by Cotran et al. (*Robbins: Pathologic Basis of Disease*, (4th ed., 1989), Ed. Robbins, 2:39–86, Philadelphia: Saunders) as the reaction of vascularized living tissue to local injury. Specific antagonists, by design, work one-on-one against substances that promote inflammation, and the efficacy of a single antagonist may be limited if more than one mediator is released during tissue injury. An agonist, a term introduced by Reuse (*Br. J. Pharmacol.*, 3, pp. 129–62 (1948)) to describe a chemical that activates biological events, would be more efficacious than an antagonist if it could suppress convergent processes initiated by more than one inflammatory mediator. The concept of drugs as anti-inflammatory agonists was discussed by Svensjo and Persson in 1985 (*Handbook of Inflammation*, Ed. Bonta, 5:51–82, Amsterdam: Elsevier).

For example, we have recently described one set of relatively small, CRF-related peptides (Wei and Thomas, *Annu. Rev. Pharmacol. Toxicol.*, 33, pp. 91–108 (1993)) and one of us has described another, related set of small CRF-related peptides (Wei, U.S. Pat. No. 5,177,060, issued Jan. 5, 1993, of common assignment herewith) for uses as anti-inflammatory agents. Thus, crude peptides corresponding to the 11-residue carboxyl terminus of human/rat CRF were found to have anti-inflammatory activity. Further characterization of the structures within the crude peptide mixture revealed that substitution of the glutamic acid residue (E) with an anisolylated glutamic acid derivative increased overall anti-inflammatory potency. The anisole derivative was apparently a by-product of the temperature-dependent Friedel-Crafts acylation reaction that occurs during hydrogen fluoride cleavage of glutamyl-containing peptides. Several peptides containing the anisolylated glutamic acid derivative were made with D-amino acid substitutions (denoted by the lower case of the single letter code). Pending U.S. patent application Ser. No. 07/925,081, filed Aug. 4, 1992, inventors Wei and Thomas, of common assignment herewith, also describes the anti-inflammatory uses of CRF-related peptides.

The search for additional compounds useful in anti-inflammatory applications continues. One of us had earlier attempted to determine if particular dynorphin compounds might merit possible development for anti-inflammatory uses. In 1986, Wei et al., *J. Pharmacol. Exp. Therap.*, 238, pp. 783–787 (1986), studied dynorphin A (1-13) and dynorphin A (1-10) amide in "neurogenic inflammation," a pathophysiological condition in which antidromic stimulation of the sensory nerve increased plasma protein leakage from small blood vessels. The potencies of dynorphin A (1-13) and dynorphin A (1-10) amide in the test system for neurogenic inflammation, measured as the median effective dose ($ED_{50}$) producing 50% inhibition of dye leakage, relative to saline-injected controls, were not high: 1.9 (1.5–2.4) mg/kg and 5.0 (3.5–7.2) mg/kg injected by the intravenous route, respectively, and thus they were not in the range of potency which merited possible development for clinical applications.

Dynorphin A (1-13) was subsequently reported to prevent edema in the anesthetized rat's paw after thermal injury at doses of 3.75 mg/kg administered intravenously (Wei and Kiang, *European J. of Pharmacology*, 168, pp. 81–86 (1989). These studies led to the conclusion that dynorphin A (1-13) lacked potency in reducing inflammation in injury models.

The endogenous opioid peptides can be divided into three distinct families (endorphins, enkephalins, and dynorphins), all contain one of two, five amino acid sequences at their amino-terminus and are present in different neuronal pathways within the central and peripheral nervous system. Molecular genetics studies have shown that these three families of opioid peptides are derived from three distinct precursors. Proopiomelanocortin (POMC) gives rise to the endorphins, as well as to adrenocorticotropic hormone (ACTH) and to the melanotropic hormones (MSH's). [Met] enkephalin, [Leu] enkephalin and a related heptapeptide and octapeptide are derived from proenkephalin. The third family is derived from prodynorphin, and includes dynorphin A, dynorphin B (also known as rimorphin) and alpha- and beta-neoendorphin.

A variety of uses for dynorphin and dynorphin-related compounds have been known for applications pertaining to combinations with narcotic analgesics or with respect to opiate activity. In addition, a compound related to the dynorphin A (1-13) compound, but without the N-terminal tyrosine and glycine (sometimes referred to as dynorphin A (3-13)), has been of recent research interest. Additional peptide fragments have been studied, such as reported by Takemori et al. in their JPET abstract of 1993 reporting dynorphin A (2-17) as suppressing naloxone-induced withdrawal and the expression of morphine tolerance in morphine dependent mice, and similar suppressive activity for dynorphin A (2-14), (2-11), and (2-8).

U.S. Pat. No. 4,361,553, issued Nov. 30, 1982, inventors Loh and Lee, sets out the sequence of the first thirteen peptides for the naturally occurring dynorphin A (containing seventeen amino acids), which had been discovered to have potent agonist properties in guinea pig ileum and mouse vas deferens. This patent describes the discovery that dynorphin, and particularly dynorphin A (1-13) has an effect in hosts tolerant to narcotic analgesic opposite to the effect which has been observed in naive animals (an inhibition of morphine or β-endorphin-induced analgesia). Thus, dynorphin A (1-13) potentiates the analgesic effect in tolerant hosts. Dynorphin was found useful in conjunction with a narcotic analgesic in order to reduce the amount of narcotic analgesic administered per dose.

U.S. Pat. No. 4,396,606, issued Aug. 2, 1983, inventor Goldstein, describes isolation of dynorphin A (1–13) which has a structure beginning at the N-terminus with tyrosine. This compound was found to be substantially more active than the enkephalins and β-endorphin in a guinea pig ileum test, and compositions containing the compound were suggested to be analgesic.

U.S. Pat. No. 4,462,941, issued Jul. 31, 1984, inventors Lee et al., describes dynorphin amide analogs with the first seven amino acids as in dynorphin A (1 -17) and 1-13, but with the next several amino acids as $AA^{8/-AA9}-AA^{10}$ wherein $AA^8$ is isoleucine, leucin, or lysine, $AA^9$ is arginine or proline, $AA^{10}$ is proline, and a carbonyl carbon at the $AA^{10}$ terminus is amidated. In tolerant animals, on the other hand, the dynorphin A (1 -10) amide analogs appears to be a more potent and selective analog than dynorphin A (1-13).

U.S. Pat. No. 4,481,191, issued Nov. 6, 1984, inventors Wei et al., describes a method for treating high blood pressure and disturbances of cardiac function by administrating dynorphin-related opioid peptides. It appears that endogenous opioid peptides condition the sensitivity of the peripheral nerves to stimuli that affect heart rate and blood pressure.

U.S. Pat. No. 4,684,624, issued Aug. 4, 1987, inventors Hosobuchi et al., describes the use of certain dynorphin-related peptides in the acid or amidated form, to treat patients suffering from cerebral ischemia. The administration of these opioid peptides to patients suffering from acute focal cerebral ischemia has been found useful in prolonging survival, and appears useful in partially reversing neurologic deficits resulting from cerebral ischemia.

SUMMARY OF THE INVENTION

Vascular leakage can result from acute inflammatory conditions, and generally indicates that tissues have been converted from a condition of balanced fluid exchange to a state in which serum and its solutes freely pass into the surrounding tissues. Substances are released, either from nerve endings or from cells within the injured tissue, that produce increased vascular permeability. Fluids and proteins in the blood then move from the vascular compartment to the tissue compartment with pain, swelling, and tissue damage as a result. Administrations in accordance with the present invention provide clinical benefits when used to limit or minimize vascular leakage for patients experiencing acute inflammation.

In one aspect of the present invention, an anti-inflammatory composition is provided that comprises an amidated peptide, including salts thereof, having the sequence
G-G-F-L-R-R-I-R-P-K-L-K-W-D-N-Q-NH₂ (SEQ ID NO:2),
Ac-R-R-I-R-P-K-L-NH₂ (SEQ ID NO:3), or
Ac-R-R-I-R-P-K-l-NH₂ (SEQ ID NO:4)
in a concentration sufficient to provide about 0.1 to about 5 mg/kg of patient body weight when administered by intravenous, intradermal, or subcutaneous injection to a patient, the peptide being in a pharmaceutically acceptable carrier.

In another aspect of the present invention, a method for treating an inflammatory condition in which vascular leakage is a problem, such as pulmonary edema, is provided in which a peptide is administered in an amount effective to decrease inflammation. The peptide is non-opiate and includes the dynorphin A (6-12) sequence. Preferred peptides (which can be in salt forms) have the sequence:
G-G-F-L-R-R-I-R-P-K-L-K-W-D-N-Q (SEQ ID NO:1),
G-G-F-L-R-R-I-R-P-K-L-K-W-D-N-Q-NH₂ (SEQ ID NO:2),
Ac-R-R-I-R-P-K-L-NH₂ (SEQ ID NO:3), or
Ac-R-R-I-R-P-K-l-NH₂.

BRIEF DESCRIPTION OF THE DRAWINGS

FIG. 1 graphically illustrates a substantial anti-inflammatory property for one of the des-Tyr dynorphin compounds in accordance with the invention, and is in contrast to both dynorphin A (1-13) and dynorphin A (1-17), which are both shown as substantially lacking potency in producing the same anti-inflammatory effect.

DETAILED DESCRIPTION OF THE PREFERRED EMBODIMENTS

The endogenous opioid peptide families (which contain the same first four amino acids at the N-terminus and either a methionine or a leucine as the fifth) interact with the principal opioid receptor subtypes (μ, κ, and ε) in brain and peripheral tissues. Based on the pharmacological activities and structural characteristics of these peptides, it is recognized that several features determine the interactions of the peptides with the opioid receptors. The requirements are (a) tyrosine residue at the amino terminus (Xie et al., *Proc. Natl. Acad. Sci. USA*, 89, pp. 4124–4128 (1992)) and (b) the ability of naloxone, an alkaloid opioid receptor antagonist, to attenuate the pharmacological activity of these peptides.

Peptides from the endorphin and dynorphin family of opioid peptides in which the tyrosine group has been removed (des-Tyr analogs) have been shown to have pharmacological activities at low doses. For example, the des-Tyr analogs of β-endorphin are postulated to have antischizophrenic effects. In animals, the des-Tyr analog of dynorphin A, also called dynorphin A (2-14 17), produces behavioral changes after intracerebroventricular administration (Walker et al., *Science*, 218, pp. 1136–1138 (1982)). In their 1993 abstract, Takemori et al. postulate that the des-Tyr analogs of dynorphin A have effects on morphine tolerance and dependence. The actions of the des-Tyr analogs of opioid peptides, by definition, are labeled "nonopioid" because the drug effects are not mediated by opioid receptors. A nonopioid drug effect is nevertheless a physiological event to the organism receiving the peptide and may be exploited for drug use.

We have discovered that des-Tyr analogues of dynorphin A have a nonopioid effect, which has not been previously recognized. This effect is that of inhibiting leakage of blood constituents into tissues after injury. This drug action is termed "anti-inflammatory" by us because an immediate manifestation of inflammation (as defined by Cotran et al., supra) is leakage of blood contents into the tissue matrix, resulting in edema and swelling. Compounds useful in accordance with the present invention for the anti-inflammatory applications do not have an N-terminal tyrosine, include the dynorphin (6-12) segment (although some substitutions are possible), and are non-opiate. These criteria are further discussed below.

Preliminary molecular modeling studies indicate that proline at the 10 position forms a loop and that the adjacent arginines, together with the hairpin, may constitute a fixed, spatial alignment necessary for activity. The particular pattern of activity observed with des-Tyr dynorphin A (or dynorphin A (2-17)), dynorphin A (1-17), and dynorphin A (1-13) indicates that a precise relationship exists among the structure of these peptides and their biological activities. For peptides, biological activity is determined by the conformation of the molecule in the cellular receptor environment. To ascertain the molecular requirements for biological activity we used techniques called computer assisted quantitative structure activity relationship (QSAR) studies and comparative molecular field analysis (CoMFA). The QSAR/CoMFA system was developed in 1988 as part of the Sybyl software program by Tripos Associates (St. Louis, Mo.), and it runs a Silicon Graphics IRIS 4D machine or equivalent. The QSAR/CoMFA program utilizes a partial least squares regression analysis to correlate the molecular fields of a molecule (the independent variable) with the biological properties, such as potency (the dependent variable). Preliminary data suggest that several features or molecular fields of the des-Tyr dynorphin A fragment determine its greater potency relative to the intact dynorphin A peptides. The modeling procedures showed that (1) the proline residue in position 10 of dynorphin A induced the formation of a hairpin loop causing the amino and carboxyl termini of the peptide to fold into close proximity of each other, (2) the constraints of the hairpin loop, in turn, set the position, spacing and character of the positive charges in the double arginine residues of dynorphin A, namely $Arg^6$ and $Arg^7$, and the relative positions of these two basic amino acids may be important for bioactivity, (3) additions to (or deletions from) the core peptide (6-12) on either end may cause conformational changes in other regions of the peptide (by twisting or turning the hairpin) and therefore, also affect bioactivity. Of the peptides tested thus far, the optimum configuration for inhibition of vascular leakage is that conferred by dynorphin A (2-17).

We postulate that the core, or essential portion, of the des-Tyr dynorphin A molecule for anti-inflammatory residues is the dynorphin A (6-12) sequence (-Arg-Arg-Ile-Arg-Pro-Lys-Leu-, SEQ ID NO:5). This core has two basic residues and two hydrophobic residues, and is of similar size (seven residues) to other prior known anti-inflammatory peptide agonists. For example, the prior known CRF (31-41) and related analogs called mystixins, neurotensin-related peptides, antiflammin 1, and VIP all have double basic residues (that is, -Arg-Lys-, -Lys-Arg-, -Arg-Arg-, or -Lys-Lys-). All also have the presence of at least two hydrophobic residues, namely leucine, isoleucine, methionine, or valine. The comparative molecular field analysis of the dynorphin A structure suggests that the conformational rigidity conferred by the proline residue is what is required for promoting anti-inflammatory action.

We believe that variations and substitutions suitable for the core for purposes such as protecting against enzymatic degradation include N-acetylated, or the introduction of a pseudopeptide bond between the first and second amino acid residues of the N-terminus. These techniques to confer resistance to enzymatic degradation are, for example, described by Lugrin et al., *Europ. J. Pharmacol.*, 205, pp. 191–198 (1991). Further, unnatural amino acids to stabilize or to increase potency and prolong duration of action are illustrated, for example, by Nestor et al., *J. Medicinal Chem.*, 31(1), pp. 65–72 (1988) and 27, pp. 320–305 (1984). Another technique for modifying the core sequence is to replace an L-amino acid residue with a D-amino acid residue. Yet another technique for making modifications is where peptide bonds have been replaced by derivatives, such as, for example, with $CH_2NH$ ($\Psi$ reduced) bonds.

In the present invention, a des-Tyr dynorphin-related compound (or a salt form thereof) is used to inhibit inflammation of a mammal's skin, mucous membranes, or where there have been (or will be) lacerations of the musculature or injury to the brain. Administration can be by intravascular, oral or topical means at dosages of between about 0,001 to 5 mg/kg body weight. However, administration is preferably by intravenous, intradermal, or subcutaneous injection with at least a single dose being given, preferably from about 0.1 to 5 mg/kg body weight, and can be up to about two hours before deliberate lacerations of the musculature (such as during abdominal or orthopedic surgery) and can be up to three days after surgery or accidental injury. Administration is most preferably via the blood stream, but local injections into injured tissues such as the muscle can be used.

Because use of the des-Tyr peptides in accordance with the invention provides the property of inhibiting vascular leakage from tissues, a number of different therapeutic applications are possible. Specific tissues for which clinical usage of these peptides may be applied include skin and mucosal membranes (eyelids, nasal membranes, oropharyngeal membranes, upper respiratory tract, esophagus, lower digestive tract), skeletal muscle, smooth muscle, cardiac muscle, blood vessels of the brain, and blood vessels of the lungs and kidneys. For example, therapeutic uses of these peptides include administration to treat thermal burns, irradiation burns, frostbite, or for other inflammatory conditions of the skin. The peptides may be used to reduce swelling, pain, and plasma extravasation. For irritants deposited on the upper airways or in chronic allergic conditions such as asthma, the peptides may be used to decrease irritancy, bronchial inflammation, edema and plasma extravasation. For lacerative or traumatic injuries to all tissues, such as might occur after knife wounds, surgical operations, and automobile accidents, the peptides may be used to reduce swelling, pain, and inflammation. For tissue infarcts, which result in tissue hypoxia, ischemic anoxia and edema, such as occur after brain strokes or myocardial infarcts, the peptides may be used to reduce passage of blood constituents into the tissue matrix and enhance survival of the remaining tissues. For preventing the actions of endogenous or exogenous chemicals that directly injure the endothelium, such as endotoxins or inflammatory mediators, resulting in the clinical condition of septic shock, the peptides may be useful in reducing the loss of blood volume. Administration may be used for preserving the integrity of the vascular tree of an organ prior to or during its removal for transplantation, such organs being kidneys, liver, or heart.

The des-Tyr dynorphin-related peptides may be administered in combination with a pharmaceutically acceptable carrier, such as isotonic saline, phosphate buffer solution or the like. Topical administration is also feasible since the peptides are relatively small.

Compositions and excipients useful for the administration of small peptides through the nasal mucosa are, for example, described by U.K. patent application No. 8719248, published Feb. 24, 1988, applicant Sandoz Limited. Topical compositions with enhanced penetration through intact skin preferably include a potentiator, many of which are described by U.S. Pat. No. 4,091,090, issued May 23, 1978, inventor Sipos.

The peptides form pharmaceutically acceptable salts and can be administered in salt form. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethane-sulfonic. Salts may also be formed with suitable organic pharmaceutically acceptable base addition salts. These organic bases form a class whose limits are readily understood by those skilled in the art. Merely for purposes of illustration, the class may be said to include mono-, di-, and trialkyamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66 (1): 1–19 (1977).

The peptides can be synthesized by various suitable chemical methods, preferably by solid phase synthesis, manual or automated, as first developed by R. B. Merrifield and described by J. M. Stewart and J. D. Young in "Solid Phase Peptide Synthesis" (1984). Chemical synthesis joins the amino acids in the predetermined sequence starting at the C-terminus. Basic solid phase methods require coupling the C-terminal protected alpha-amino acid to a suitable insoluble resin support. The described peptides require benzyhydrylamine (BHA) or 4-methylbenzyhydrylamine (MBHA) resins to produce the C-terminal amide upon completion. Amino acids for synthesis require protection on the alpha-amino group to ensure proper peptide bond formation with the preceding residue (or resin support). Following completion of the condensation reaction at the carboxyl end, the alpha-amino protecting group is removed to allow the addition of the next residue. Several classes of alpha-protecting groups have been described, see J. M. Stewart and J. D. Young in "Solid Phase Peptide Synthesis" (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid side-chain functional groups require blocking until the synthesis is completed. The complex array of functional blocking groups, along with strategies and limitations to their use, have been reviewed by M. Bodansky in "Peptide Synthesis" (1976), and, J. M. Stewart and J. D. Young in "Solid Phase Peptide Synthesis" (1984).

Solid phase synthesis is initiated by the coupling of the described C-terminal alpha-protected amino acid residue. Coupling requires activating agents, such as dicyclohexylcarbodiimide (DCC) with or without 1-hydroxybenzo-triazole (HOBT), diisopropylcarbodiimide (DIIPC), or ethyldimethylaminopropylcarbodiimide (EDC).

Particularly preferred des-Tyr dynorphin-related compounds for anti-inflammatory uses in accordance with this invention are dynorphin A (2-17), dynorphin A (2-17) amide, and two des-Tyr dynorphin-related fragments, as set out in Table 1.

TABLE 1

| Preferred Embodiments for Use in Accordance with Invention | EMBODIMENT NO: |
| --- | --- |
| G-G-F-L-R-R-I-R-P-K-L-K-W-D-N-Q | 1 |
| G-G-F-L-R-R-I-R-P-K-L-K-W-D-N-Q-NH$_2$ | 2 |
| Ac-R-R-I-R-P-K-L-NH$_2$ | 3 |
| Ac-R-R-I-R-P-K-l-NH$_2$ | 4 |

The preferred embodiments of SEQ ID NO:1 (Embodiment NO:1) and SEQ ID NO:2 (Embodiment NO:2) are dynorphin A (2-17) and amidated dynorphin A (2-17), respectively. The preferred embodiment of SEQ ID NO:3 (Embodiment NO:3) includes the dynorphin A (6-12) sequence, but has an acetylated amino-terminus and an amidated carboxyl terminus, while the preferred embodiment of Embodiment NO:4 additionally has an amino acid replacement of D-leucine for leucine. Amidation is believed to increase potency.

In a direct comparison of dynorphin A analogs with an amide or a carboxyl moiety on the C-terminus, we found that the amidated form was about two times more potent than the carboxyl form. Thus, the $ED_{50}$ value of D-Ala$^2$-dynorphin A (2-17) amide was 0.65 mg/kg i.v. compared to a value of 1.2 mg/kg i.v. for D-Ala$^2$-dynorphin A (2-17). Similar results were obtained for D-Ala$^2$-dynorphin A (1-17) amide, with an $ED_{50}$ value of 0.5 mg/kg i.v. versus a value of 1.0 mg/kg i.v. for D-Ala$^2$-dynorphin A (1-17). From these results, we conclude that the amidated peptide is likely to have greater potency than the peptide with the natural carboxyl terminus.

Aspects of the invention will now be exemplified by the following additional examples, which are understood to be illustrative and not limiting. These examples involve the use of bioassays.

In defining the "anti-inflammatory" properties of peptides, it is helpful to explicitly state which stage of inflammation is being investigated and to define the significance of the experimental models. Traditionally, pharmacologists have been interested in chronic inflammation because of its importance in persistent conditions such as arthritis, asthma, and related diseases. Bioassays for agents that suppress the acute phase of inflammation have a shorter time course and are, in principle, faster to conduct, because simple nonselective methods of traumatic injury can be utilized to produce immediate indices of tissue response. The two bioassays described below are useful as rapid screening tools. The first measures heat-induced swelling and edema. The second considers the measurement of a drug's actions against epinephrine-induced pulmonary edema. These bioassays yield information about the types of vascular beds acted upon by the drug. These bioassays are conducted in the intact animal. The results are applicable to clinical conditions in humans where there is acute injury to tissues.

In one bioassay, dynorphin A (2-17), synthesized by standard solid phase methods, was dissolved in sterile saline and injected intravenously via a branch of the femoral vein at various doses into an anesthetized rat. Ten minutes later a hind paw was immersed in 58° C. water for one minute. Thirty minutes after exposure to heat, the paw was removed at the ankle joint and weighed. The percent increase in weight of the heated paw relative to the unheated paw was taken as the index of inflammatory thermal edema. The general principles of this method have been discussed by Wei and Thomas, *Ann. Rev. of Pharmacol. and Toxicol.*, 33, pp. 91–108 (1993).

In another bioassay, either saline (1 mg/kg) or dynorphin A (2-17) (0.2 mg/kg) was injected i.v. ten minutes before epinephrine bitartrate 30 µg/kg i.v. This bioassay is a model of pulmonary edema. Epinephrine, which constricts blood vessels, rapidly shifts the blood volume from the muscles and viscera into the lung. The increase in hydrostatic pressure in the blood vessels of the lung breaks the endothelial barriers and the blood then enter the air-spaces of the lung and the water contents (and weights) of the lung go up. In normal untreated rats, the lung weights are about 0.5% of body weight, or, for rats weighing 213±3 gm, equal to 1.06 gm. Thirty minutes after epinephrine bitartrate, the lung weights increased to 1.90±0.16 gm and the animals manifested labored breathing and pink froth could by found in the trachea when it was cut open. After treatment with dynorphin A (2-17) the lung weights were 1.32±0.11 gm. The results were highly significant (P<0.01) and indicated that dynorphin A (2-17) inhibited the lung edema induced by epinephrine.

Vascular leakage is an inflammatory response to any stimuli that produces injury in living tissues that is perfused by blood. To further demonstrate the anti-inflammatory actions of a des-Tyr dynorphin A peptide, we injected anesthetized rats with substance P, a peptide that acts as a stimulant of inflammatory processes. In rats pretreated with Evans blue dye (which binds to blood proteins and serves as a marker or label for vascular leakage), substance P, injected 40 µg/kg subcutaneously, elicits a pronounced bluing of tissues (skin and muscle) at the site of injection and in other vascularized areas of the body (pinna, esophagus, trachea, bladder, etc.). In animals pretreated with dynorphin A (2-17) (1 mg/kg) i.v. 10 minutes before substance P, the bluing of the tissues mentioned above (which is indicative of the inflammatory response), was suppressed (N=4 pairs of animals were tested). The effects were apparent to the naked eye and were confirmed by microscopic examination of the tissues. These results, coupled with the observations on heat-induced and epinephrine-induced edema, clearly show that the anti-inflammatory property of dynorphin A (2-17) is a generalized inhibitory action on vascular leakage.

Des-Tyr dynorphin A at a dose of 0.2 mg/kg i.v. produced a slight fall in blood pressure lasting 10–15 minutes, after which mean arterial pressure returned to baseline. Rats receiving this dose appeared to be well oxygenated; there was no evidence of cyanosis and no gut movements that might be indicative of hypoxic conditions in the gut.

We also synthesized the two peptides illustrated in Table 1 as SEQ ID NO:3 Embodiment NO:3 and Embodiment NO:4. Peptides were made by solid phase methods on either a p-methylbenzyhydrylamine (for amidated peptides) or chloromethylpolystyrene resin using the procedures as described in standard texts (Merrifield, 1963; Stewart and Young, 1984). Acetylation of the amino terminus was conducted using acetic anhydride as the source of the acetyl group. Cleavage and deprotection of the assembled peptide from the resin was carried out with hydrogen fluoride in 10% anisole and 1% (by volume) methylethylsulfide at 0° C. for 1 hour. The products were purified by gel filtration and cation-exchange chromatography. The purity of the final products was determined by high-performance liquid chromatography and the identity of the purified products was verified by amino acid analysis with a H/P Amino Quant amino acid analyzer.

These peptides were found to be biologically active in reducing thermal edema at $ED_{50}$ values of 1.4 (0.6–3.7) and 2.2 (1.2–4.1) mg/kg, injected intravenously. The anti-inflammatory effects of SEQ ID NO:1 at 0.5 mg/kg i.v. and of SEQ ID NO:3 at 3 mg/kg i.v., were not antagonized by the opioid receptor antagonist naloxone, 4 mg/kg i.v.

Anesthetized rats were injected intravenously (i.v.) with saline (1 ml/kg) or naloxone hydrochloride (4 ml/kg) 5 minutes prior to i.v. injection with saline (1 mg/kg), dynorphin A (2-17) (0.5 mg/kg), or N-acetyldynorphin A (6-12)-amide (3 mg/kg). Ten minutes after the second injection, the rat's hind paw was immersed in 58° C. water for one minute and 30 minutes later the animals were euthanized and the heated and unheated paw weights were measured. After saline/saline or naloxone HCl/saline, the percent increase in the weight of the heated paw, relative to the unheated paw, were 104±10% and 98±9%, respectively. The percent increases for the saline/dynorphin A (2-17) and naloxone HCl/dynorphin A (2-17) groups were 26±6% and 26±5%, respectively. The percent increases for the saline/N-acetyl-dynorphin A (6-12) amide and naloxone HCl/N-acetyl-dynorphin A (6-12) amide groups were 21±3% and 27±12%, respectively.

These results clearly show that the anti-inflammatory effects of the des-Tyr dynorphin A peptides were not antagonized by a large dose of naloxone and, coupled with the fact that these peptides do not contain tyrosine, illustrate that the drug action is independent of activation of opioid receptors.

Turning to FIG. 1, dose response relationships are shown for des-Tyr dynorphin A. This data further shows the unique nonopioid anti-inflammatory property of a des-Tyr dynorphin A peptide by comparing the potencies of dynorphin A (2-17), dynorphin A (1-13), and dynorphin A (1-17). The dynorphin A (2-17) was a potent inhibitor of thermal edema with a clinically significant median effective dose ($ED_{50}$) of 0.15 (0.09–0.24) mg/kg i.v. By contrast, the $ED_{50}$ of dynorphin A (1-13) and dynorphin A (1-17) were 3.2 (1.9–5.5) mg/kg i.v. and 1.7 (1.2–2.4) mg/kg i.v., respectively, values which are at least an order of magnitude less potent than the des-Tyr peptide, and which are so low as to not be sufficient to proceed with clinical evaluation.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: NO (iv) ANTI-SENSE: NO (xi) SEQUENCE DESCRIPTION: SEQ ID NO:1:

Gly Gly Phe Leu Arg Arg Ile Arg Pro Lys Leu Lys Trp Asp Asn Gln
1               5                   10                  15

(2) INFORMATION FOR SEQ ID NO:2:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

Gly Gly Phe Leu Arg Arg Ile Arg Pro Lys Leu Lys Trp Asp Asn Gln
1               5                   10                  15

(2) INFORMATION FOR SEQ ID NO:3:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

Arg Arg Ile Arg Pro Lys Leu
1               5

(2) INFORMATION FOR SEQ ID NO:5:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:5:

Arg Arg Ile Arg Pro Lys Leu
1               5

It is to be understood that while the invention has been described above in conjunction with preferred specific embodiments, the description and examples are intended to illustrate and not limit the scope of the invention, which is defined by the scope of the appended claims.

It is claimed:

1. An anti-inflammatory composition comprising:
an amidated peptide or salt thereof having the sequence Ac-R-R-I-R-P-K-L-NH$_2$ (SEQ ID NO:3), or
Ac-R-R-I-R-P-K-l-NH$_2$ in a concentration sufficient to provide about 0.1 to about 5 mg/kg patient body weight when administered by intravenous, intradermal, or subcutaneous injection to a patient, the peptide being in a pharmaceutically acceptable carrier.

2. A method for treating a patient for an acute inflammatory condition in which vascular leakage is a factor comprising:

administering to the patient an amount of a peptide, including salts thereof, in an amount effective to decrease inflammation, the peptide administered having a core sequence, the core sequence having -Arg-Arg-Ile-Arg-Pro-Lys-Leu- (SEQ ID NO:5), the peptide being non-opiate.

3. The method as in claim 2 wherein the acute inflammatory condition is pulmonary edema.

4. The method as in claim 2 or 3 wherein the administering is by intravenous, intradermal, or subcutaneous injection.

5. The method as in claim 4 wherein the peptide is administered in combination with a pharmaceutically acceptable carrier and is optionally modified to convey resistance to enzymatic degradation or to enhance stability.

6. The method as in claim 2 wherein the administering is an injected or infused dose of between about 0.1 to about 0.5 mg/kg of patient body weight.

7. The method as in claim 2 wherein the peptide or salt thereof has the sequence
G-G-F-L-R-R-I-R-P-K-L-K-W-D-N-Q (SEQ ID NO:1),
G-G-F-L-R-R-I-R-P-K-L-K-W-D-N-Q-NH$_2$ (SEQ ID NO:2),
Ac-R-R-I-R-P-K-L-NH$_2$ (SEQ ID NO:3), or
Ac-R-R-I-R-P-K-l-NH$_2$.

8. A method for treating inflammatory conditions of tissue comprising:

exposing the tissue to an amidated peptide or salt thereof having the sequence
G-G-F-L-R-R-I-R-P-K-L-K-W-D-N-Q (SEQ ID NO:1),
G-G-F-L-R-R-I-R-P-K-L-K-W-D-N-Q-NH$_2$ (SEQ ID NO:2),
Ac-R-R-I-R-P-K-L-NH$_2$ (SEQ ID NO:3 ), or
Ac-R-R-I-R-P-K-l-NH$_2$ in combination with a pharmaceutically acceptable carrier.

9. The method as in claim 8 wherein the tissue includes an organ prior to or during its removal for transplantation.

10. The method as in claim 8 wherein the tissue is exposed about two hours before injury and up to about three days thereafter.

* * * * *